United States Patent [19]

Seki et al.

[11] Patent Number: 5,416,120
[45] Date of Patent: May 16, 1995

[54] VASCULAR HYPERTROPHY INHIBITOR

[75] Inventors: Jiro Seki, Kobe; Yasuko Kato, Nishinomiya; Mie Sado, Himeji, all of Japan

[73] Assignee: Fujisawa Pharmaceutical Co., Ltd., Osaka, Japan

[21] Appl. No.: 182,179

[22] PCT Filed: Jul. 31, 1992

[86] PCT No.: PCT/JP92/00972
§ 371 Date: Feb. 4, 1994
§ 102(e) Date: Feb. 4, 1994

[87] PCT Pub. No.: WO93/03715
PCT Pub. Date: Mar. 4, 1993

[30] Foreign Application Priority Data

Aug. 13, 1991 [JP] Japan .................. 3-288244

[51] Int. Cl.$^6$ ........................................ A61K 31/15
[52] U.S. Cl. .................................................. 514/626
[58] Field of Search ........................................ 514/626

[56] References Cited

FOREIGN PATENT DOCUMENTS 0113106  7/1984  European Pat. Off. .

OTHER PUBLICATIONS

Yamada et al Medline abstract of Br. J. Pharmacol. 103(3): 1713-8 Jul. 1991.
Shibata et al Medline Abstract of J. Cardiovasc. Pharmocol. 17(3):508-518 Mar. 1991.
Hino et al (I) Cell. Sci. (9):704-709(1990) GA. 115:21440B.
Hino et al (II) J. Antibiot (Tokyo) 42 (11):1578-1583 Nov. 1989 Medline Abstract.
Okamoto et al E.P. 113106 (Jul. 11, 1984) GA. 101:170730J.
Fujisawa Pharm. Co. Ltd JP 60/68390 (Aug. 31, 1985) Derwent Abstract.
Eur. J. Pharmacol., vol. 183, No. 4, pp. 1292-1293, (1990), M. Ohtsuka, et al., "Cardiovascular Activity of FK409, A New Drug For Ischemic Heart Diseases, On Dog In Vitro And In Vivo Preparations".

*Primary Examiner*—Shep K. Rose
*Attorney, Agent, or Firm*—Oblon, Spivak, McClelland, Maier, & Neustadt

[57] ABSTRACT

This invention relates to a vascular hypertrophy inhibitor containing a compound of the formula

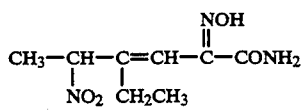

or its pharmaceutically acceptable salt as an active ingredient. This composition produces excellent effects as a vascular hypertrophy inhibitor.

6 Claims, No Drawings

VASCULAR HYPERTROPHY INHIBITOR

TECHNICAL FIELD

This invention relates to a vascular hypertrophy inhibitor and more particularly to a vascular hypertrophy inhibitory composition comprising a compound of formula (I)

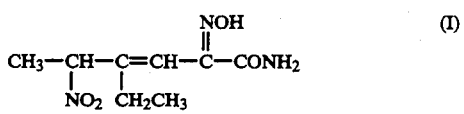

or a pharmaceutically acceptable salt thereof as an active ingredient.

BACKGROUND ART

It is known that angioplasty, arterial bypass surgery, organ transplantation, etc. frequently entail a hypertrophy and occlusion of the blood vessel owing to, inter alia, proliferation of vascular smooth muscle cells. Though much study is undergoing for finding a useful drug for the prevention and cure of the condition (e.g. J P Kohyo H3-500660), no effective drug has been discovered as yet.

Inspired by this demand for drugs effective for the prevention and cure of vascular hypertrophy, the inventors of this invention did much research and discovered that a compound of the above formula (I), which is already known to have vasodilatory and antithrombotic activities, is capable of inhibiting vascular hypertrophy. Further research has culminated in the perfection of this invention.

DISCLOSURE OF INVENTION

The vascular hypertrophy inhibitory composition of this invention comprises a compound of the above formula (I) or a pharmaceutically acceptable salt thereof as an active ingredient.

The vascular hypertrophy inhibitory composition of the invention finds application as a prophylactic/therapeutic drug for vascular hypertrophy, that is to say the thickening and occlusion of blood vessels owing, inter alia, to the proliferation of vascular smooth muscle cells which occur frequently following various operations in man and animals.

The pharmaceutically acceptable salt of compound (I) for use as the active ingredient in this invention includes salts with inorganic or organic bases such as alkali metal salts, e.g. sodium salt, potassium salt, etc., alkaline earth metal salts, e.g. calcium salt etc., ammonium salt, and organic amine salts such as ethanolamine salt, triethylamine salt, dicyclohexylamine salt and so on.

While the compound (I) for use as the active ingredient in this invention includes its stereoisomers, the representative species is $(\pm)$-(E)-4-ethyl-2-[(E)-hydroxyimino]-5-nitro-3-hexenamide (which is hereinafter referred to as FK409).

The vascular hypertrophy inhibitory composition of this invention is of value as an inhibitor of the hypertrophy (e.g. which can be a cause for restenosis after percutaneous coronary angioplasty) and obstruction of the blood vessel which occur owing, in the main, to the proliferation of vascular smooth muscle cells following angioplasty (e.g. percutaneous coronary angioplasty), arterial bypass procedure, organ transplantation and other operations or a prophylactic/therapeutic drug for vascular hypertrophy and obstruction (or an inhibitor of vascular smooth muscle cell proliferation). The effectiveness of this invention is now shown by way of experimental data.

Test Example: Inhibitory effect on intimal hypertrophy following balloon catether-associated carotid artery endothelial injury in rats Method: The test was performed in accordance with the method of Close et al. (Lab. Invest. 49, 208, 1983), as follows.

Male SD rats weighing 400–500 g were used. Each rat was anesthetized with pentobarbital sodium and the cervical region was opened. A balloon catheter (Fogarty, 2F) was inserted from the left external carotid artery to the orgin of the common carotid artery. The balloon was then inflated with physiological saline until a slight resistance was felt. The inflated balloon was pulled back as it was to the external carotid artery so as to injure the arterial intima. This operation was repeated 3 times, after which the catheter was withdrawn and the external carotid artery was ligated. After 14 days, the chest was opened under pentobarbital anesthesia and following perfusion with heparin-containing physiological saline (20 units/ml) from the left ventricle, the left common carotid artery was excised and fixed in neutralized formalin. The fixed carotid artery was orcein-stained and microphotographed and the sectional area of the media and that of the hypertrophic portion of the intima were measured by means of an image analyzer (LUZEX2D).

The daily administration of the test drug was commenced 2 days preceding the operation and continued till the 13th postoperative day.

The intimal thickening inhibitory activity of the drug was determined using the following equation. Intimal thickening inhibition rate $(\%) = (1 - T/C) \times 100$ (where T is the area of the thickened portion of the rat intima in the drug treatment group and C is the corresponding value in the control (vehicle) group).

Results:

The results are shown in the following table.

| Drug | Dosage | n | Area of hypertrophic intima (mm$^2$) | % Inhibition |
|---|---|---|---|---|
| Control | | 6 | 0.168 ± 0.026 | — |
| FK409 | 1 mg/kg × 2, po | 5 | 0.114 ± 0.027 | 32% |
| | 10 mg/kg × 2, po | 5 | 0.054 ± 0.013** | 68% |
| Control | | 6 | 0.154 ± 0.016 | — |
| Aspirin | 32 mg/kg × 1, po | 6 | 0.153 ± 0.011 | 1% |
| Control | | 7 | 0.173 ± 0.017 | — |
| Isradipine | 3.2 mg/kg × 1, sc | 6 | 0.135 ± 0.020 | 22% |
| Control | | 8 | 0.172 ± 0.022 | — |
| Isosorbide dinitrate | 100 mg/kg × 2, po | 6 | 0.152 ± 0.022 | 12% |

$P < 0.01$

The vascular hypertrophy inhibitory composition of this invention can be used as a solid, semisolid or liquid pharmaceutical preparation containing the active substance of the invention as provided by blending the substance with an organic or inorganic carrier or vehicle suited for topical, oral or parenteral administration. The active ingredient substance can be blended with any nontoxic, pharmaceutically acceptable carriers that are commonly used in various dosage forms including tablets, pellets, capsules, suppositories, injections, solutions, emulsions, suspensions and so on. Among the carriers that can be used are water, glucose, lactose, gum arabic, gelatin, mannitol, starch paste, magnesium trisilicate, talc, corn starch, keratin, colloidal silica, potato starch, urea and other solid, semisolid or liquid pharmaceutically acceptable vehicles. In addition, adjuvants, stabilizers, thickeners, coloring agents and perfumes may be incorporated. The pharmaceutical preparation may contain a preservative or bacteriostat for maintaining the activity of its active ingredient. In such a preparation, the active ingredient should occur in a sufficient amount to produce the desired therapeutic effect according to the stage or severity of the disease.

For application of this vascular hypertrophy inhibitor to man, it is preferably administered intravenously, intramuscularly or orally. The dosage or therapeutically effective amount of the objective compound of the invention varies with each patient's age and condition but the daily dose is usually about 0.1–100 mg and the unit dose is 10 mg, 50 mg, 100 mg, 250 mg or 500 mg on the average.

Industrial applicability

As described above, the vascular hypertrophy inhibitor of this invention is of use as a prophylactic/therapeutic drug for vascular hypertrophy for inhibiting the thickening and obstruction of blood vessels which occur frequently following various operations.

We claim:

1. A method of treating vascular hypertrophy, comprising administering a compound of the formula

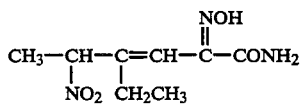

or a pharmaceutically acceptable salt thereof to a patient in need thereof following an operation selected from the group consisting of angioplasty, arterial bypass surgery and organ transplantation.

2. The method of claim 1, wherein the blood vessels of said patient are thickened and obstructed.

3. The method of claim 1, wherein vascular smooth muscle cells are proliferating or have proliferated in said patient.

4. The method of claim 1, wherein said operation is angioplasty.

5. The method of claim 1, wherein said operation is arterial bypass surgery.

6. The method of claim 1, wherein said operation is organ transplantation.

* * * * *